United States Patent
Dogrusoz et al.

(10) Patent No.: US 12,056,285 B2
(45) Date of Patent: Aug. 6, 2024

(54) ELECTRODES FOR GESTURE RECOGNITION

(71) Applicant: Apple Inc., Cupertino, CA (US)

(72) Inventors: Kaan E. Dogrusoz, Santa Clara, CA (US); Ali Moin, San Mateo, CA (US); Benjamin J. Grena, San Francisco, CA (US); Erdrin Azemi, San Mateo, CA (US); Joseph Cheng, Cupertino, CA (US); Lia M. Uesato, San Jose, CA (US); Daniel A. Podhajny, Morgan Hill, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/823,870

(22) Filed: Aug. 31, 2022

(65) Prior Publication Data

US 2023/0105223 A1   Apr. 6, 2023

Related U.S. Application Data

(60) Provisional application No. 63/261,656, filed on Sep. 24, 2021.

(51) Int. Cl.
  *G06F 3/01*   (2006.01)
  *A61B 5/00*   (2006.01)
  *A61B 5/279*  (2021.01)

(52) U.S. Cl.
  CPC .............. *G06F 3/017* (2013.01); *A61B 5/279* (2021.01); *A61B 5/681* (2013.01)

(58) Field of Classification Search
  CPC ........ G06F 3/017; G06F 1/163; G06F 1/1679; G06F 1/1684; G06F 3/014; G06F 3/015;
  (Continued)

(56) References Cited

U.S. PATENT DOCUMENTS

| | | | |
|---|---|---|---|
| 10,459,495 B2 | 10/2019 | Griffin | |
| 10,806,375 B2 | 10/2020 | Ortega et al. | |
| (Continued) | | | |

FOREIGN PATENT DOCUMENTS

| | | |
|---|---|---|
| CN | 103777752 A | 5/2014 |
| CN | 211674230 U | 10/2020 |
| WO | 2019/043147 A1 | 3/2019 |

OTHER PUBLICATIONS

Extended European Search Report received for European Patent Application No. 22195948.9, dated Feb. 13, 2023, 8 pages.

*Primary Examiner* — Grant Sitta
(74) *Attorney, Agent, or Firm* — Kubota & Basol LLP

(57) ABSTRACT

Electrodes that can be formed in a flexible band of a wrist-worn device to detect hand gestures are disclosed. Multiple rows of electrodes can be configured to detect electromyography (EMG) signals produced by activity of muscles and tendons. The band can include removable electrical connections (e.g., pogo pins) to enable the electrode signals to be routed to processing circuitry in the housing of the wrist-worn device. Measurements between signals from the active electrodes and one or more reference electrodes can be obtained to capture EMG signals at a number of locations on the band. The measurement method and mode of operation (lower power coarse detection or higher power fine detection) can determine the location and number of electrodes to be measured. These EMG signals can be processed to identify hand movements and recognize gestures associated with those hand movements.

25 Claims, 9 Drawing Sheets

(58) Field of Classification Search
CPC ....... A61B 5/279; A61B 5/681; A61B 5/0533; A61B 5/1116; A61B 5/1123; A61B 5/296; A61B 5/313; A61B 5/397
See application file for complete search history.

(56) References Cited

U.S. PATENT DOCUMENTS

| | | | |
|---|---|---|---|
| 11,026,628 B1* | 6/2021 | Bruinsma | A61B 5/332 |
| 11,331,045 B1* | 5/2022 | Moschella | A61B 5/389 |
| 2008/0077039 A1* | 3/2008 | Donnett | A61B 5/0006 |
| | | | 600/544 |
| 2011/0306892 A1* | 12/2011 | Kim | A61B 5/25 |
| | | | 600/509 |
| 2012/0188158 A1 | 7/2012 | Tan et al. | |
| 2012/0232369 A1* | 9/2012 | Kim | A61B 5/30 |
| | | | 600/372 |
| 2013/0261423 A1* | 10/2013 | Herrala | A61B 5/389 |
| | | | 600/546 |
| 2014/0148657 A1* | 5/2014 | Hendler | A61B 5/0095 |
| | | | 600/545 |
| 2014/0257129 A1 | 9/2014 | Choi et al. | |
| 2016/0007876 A1* | 1/2016 | Yoshioka | G06F 3/015 |
| | | | 600/384 |
| 2017/0123487 A1 | 5/2017 | Hazra et al. | |
| 2019/0076042 A1* | 3/2019 | Takayama | A61B 5/296 |
| 2019/0290152 A1* | 9/2019 | Bronstein | A61B 5/0042 |
| 2021/0369134 A1* | 12/2021 | Li | A61B 5/6802 |
| 2022/0087615 A1* | 3/2022 | Lee | A61B 5/7225 |
| 2022/0326762 A1* | 10/2022 | Andersen | B25J 13/086 |

* cited by examiner

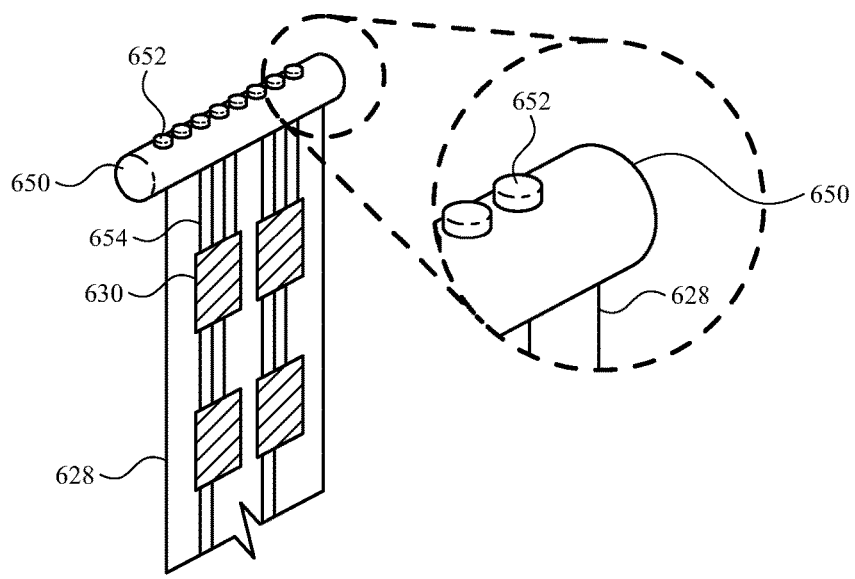
FIG. 6A
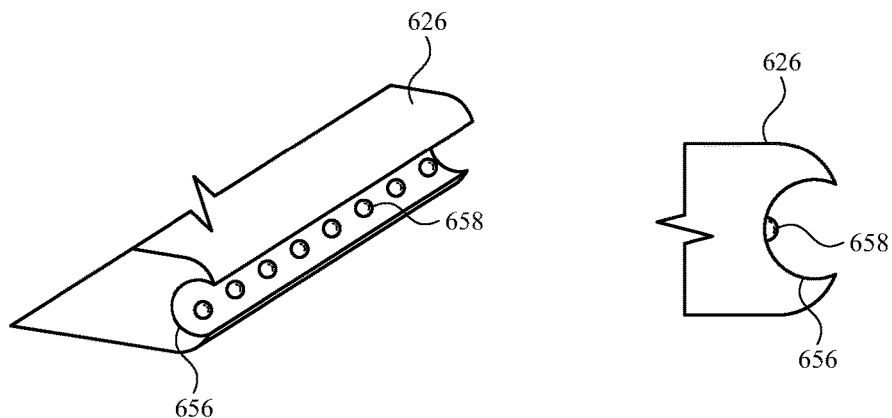
FIG. 6B
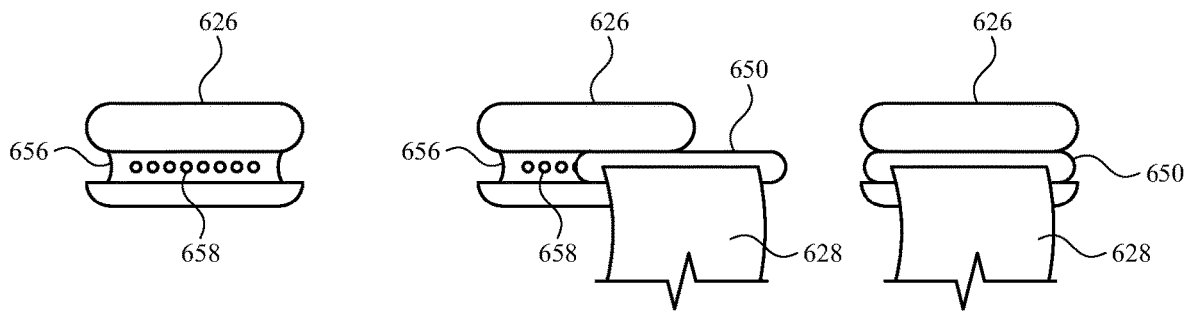
*FIG. 6C-1*  *FIG. 6C-2*  *FIG. 6C-3*

ELECTRODES FOR GESTURE RECOGNITION

CROSS-REFERENCE TO RELATED APPLICATIONS

This application claims the benefit of U.S. Provisional Application No. 63/261,656, filed Sep. 24, 2021, the content of which is incorporated herein by reference in its entirety for all purposes.

FIELD OF THE DISCLOSURE

This relates generally to gesture recognition, and more particularly to electrodes formed in a flexible band and used to detect gestures performed by a user.

BACKGROUND OF THE DISCLOSURE

Many types of input can be provided for performing operations in a computing system, such as buttons or keys, mice, trackballs, joysticks, touch sensor panels, touch screens and the like. In addition, other types of input such as audio input (e.g., voice commands), accelerometer input (e.g., device motion, shaking, etc.) and user gestures can also be provided as inputs. In particular, a person's physical motions, such as eye gaze, body movement and the like can be detected and tracked over time as inputs to the computing system. Hand gestures, in particular, can be detected by touch or proximity sensors in a touch sensing panel. However, these sensors generally have limited detection range, and therefore the hand gestures must be performed in close proximity to the panel. In some embodiments, these gestures can be detected by one or more cameras in communication with the computing system that are able to track the user's gestures and interpret them as inputs. However, camera-based systems have line of sight limitations, and require complex hardware and image processing. In other embodiments, handheld or wearable devices such as wands, controllers, or gloves can be employed to track user gestures. However these devices are not commonly worn or used, and are therefore less socially acceptable.

SUMMARY OF THE DISCLOSURE

Examples of the disclosure are directed to electrodes (textile or non-textile) that can be formed in (e.g., woven, knitted, braided, embroidered, intertwined, fabricated, laminated, etc.) a flexible band of a watch or other wrist-worn device to detect hand gestures. In some examples, the electrodes can be configured to detect electromyography (EMG) signals, which is the electrical activity that results from the contraction of muscles. In some examples, the electrodes can detect EMG signals that are produced by activity of the flexor and extensor muscles and tendons in the forearm and wrist of a user. To detect the EMG signals, multiple rows of electrodes and conductive wiring can be formed in the band of a watch or other wrist-worn device. In some examples, the band can include removable electrical connections (e.g., pogo pins) to enable the electrode signals to be routed to processing circuitry in the housing of the wrist-worn device. The signals from one or more of these electrodes can be utilized as a reference electrode, and measurements between the signals from the active electrodes and the one or more reference electrodes can be obtained to capture EMG signals at a number of locations on the band, as produced by the muscles and tendons in the user's forearm and/or wrist. These EMG signals can be processed to identify hand movements such as hand flexion, extension, pronation, supination, radial deviation, and ulnar deviation, and recognize gestures associated with those hand movements. The device can be operated in different power modes using fewer or more electrodes for coarse and fine gesture detection.

BRIEF DESCRIPTION OF THE DRAWINGS

FIG. 6A illustrates some details of contacts in a connector according to some examples of the disclosure.

FIG. 6B illustrates some details of a receptacle in a housing for receiving a connector according to some examples of the disclosure.

FIGS. 6C-1 to 6C-3 illustrates the engagement of a connector of a band with a housing according to some examples of the disclosure.

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

Examples of the disclosure are directed to electrodes (textile or non-textile) that can be formed in (e.g., woven, knitted, braided, embroidered, intertwined, fabricated, laminated, etc.) a flexible band of a watch or other wrist-worn device to detect hand gestures. In some examples, the electrodes can be configured to detect electromyography (EMG) signals, which is the electrical activity that results from the contraction of muscles. In some examples, the electrodes can detect EMG signals that are produced by activity of the flexor and extensor muscles and tendons in the forearm and wrist of a user. To detect the EMG signals, multiple rows of electrodes and conductive wiring can be formed in the band of a watch or other wrist-worn device. In some examples, the band can include removable electrical connections (e.g., pogo pins) to enable the electrode signals to be routed to processing circuitry in the housing of the wrist-worn device. The signals from one or more of these electrodes can be utilized as a reference electrode, and measurements between the signals from the active electrodes and the one or more reference electrodes can be obtained to capture EMG signals at a number of locations on the band, as produced by the muscles and tendons in the user's forearm and/or wrist. These EMG signals can be processed to identify hand movements such as hand flexion, extension, pronation, supination, radial deviation, and ulnar deviation, and recognize gestures associated with those hand movements. The device can be operated in different power modes using fewer or more electrodes for coarse and fine gesture detection.

Figure 1:
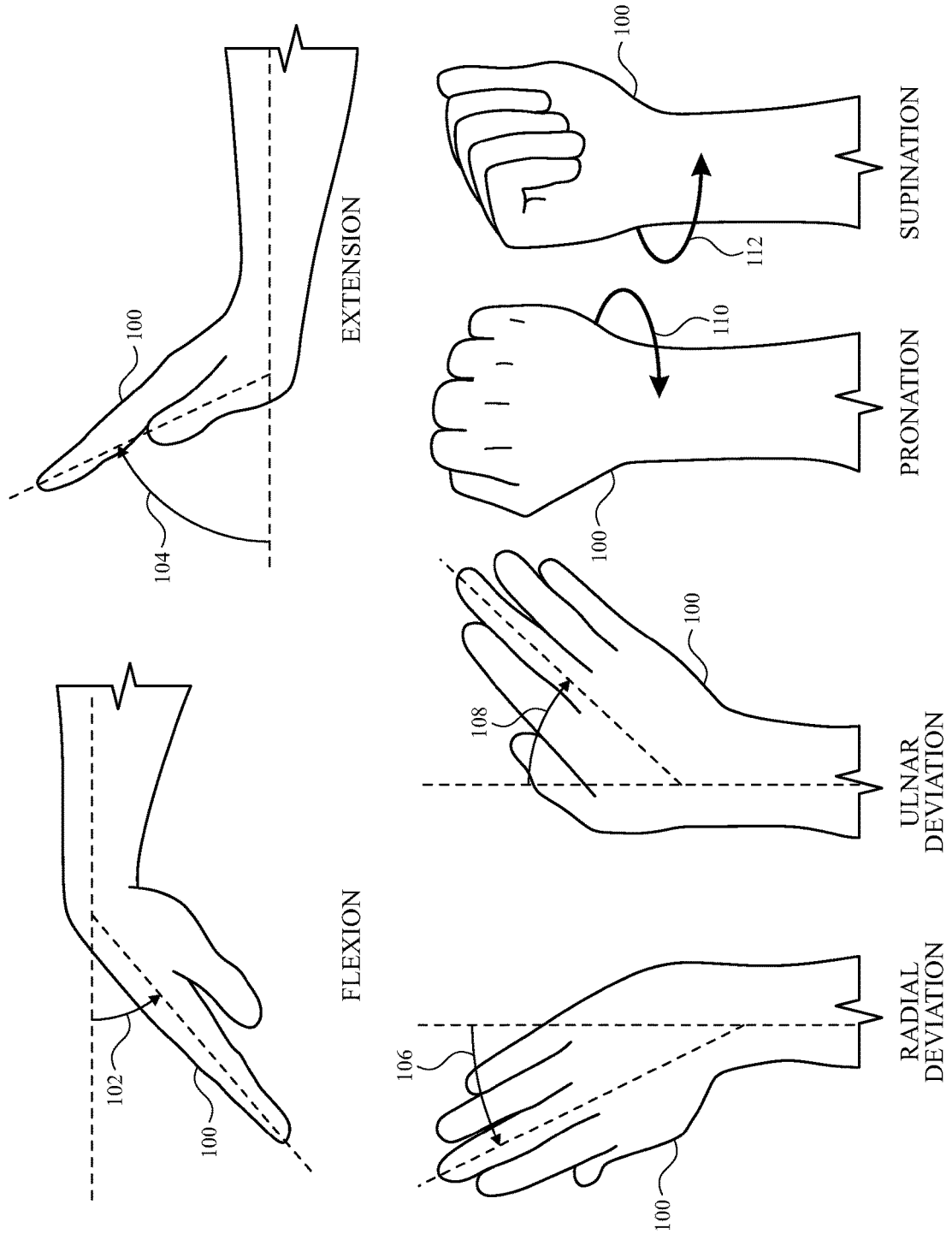
FIG. 1 illustrates various hand movements that can be performed as part of a hand gesture according to some examples of the disclosure.

FIG. 1 illustrates various hand movements that can be performed as part of a hand gesture according to some examples of the disclosure. For example, hand 100 can perform one or more of wrist flexion 102, extension 104, radial deviation 106, ulnar deviation 108, pronation 110, or supination 112. Any one of these movements, or a combination of these movements, can be performed as a gesture.

Figure 2:
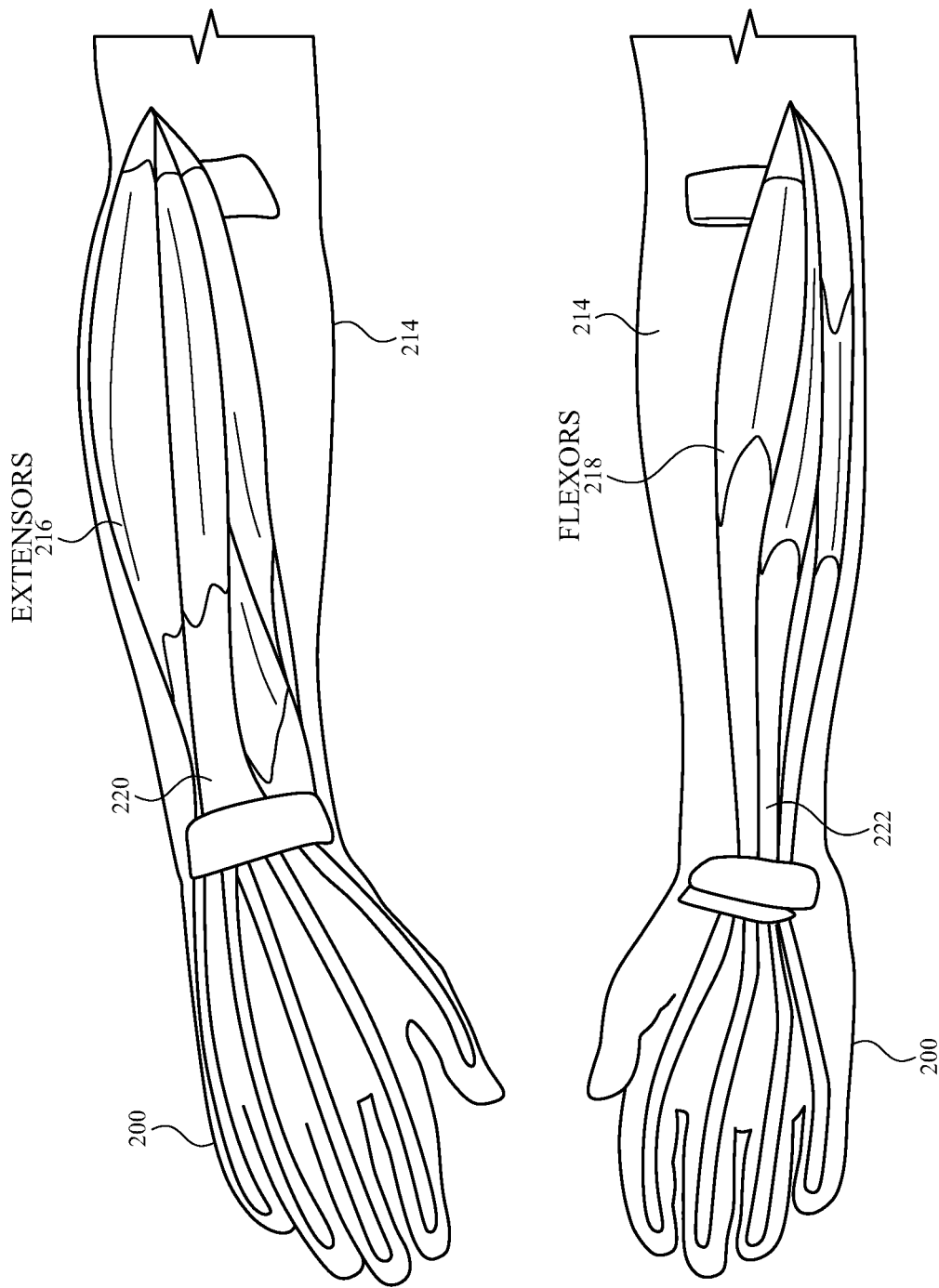
FIG. 2 illustrates various muscles and tendons that can be activated to perform the various hand movements of FIG. 1 according to some examples of the disclosure.

FIG. 2 illustrates various muscles and tendons that can be activated to perform the various hand movements of FIG. 1 according to some examples of the disclosure. Forearm 214 includes forearm extensor muscles 216 and flexor muscles 218, and wrist extensor tendons 220 and flexor tendons 222. When these muscles and tendons contract or extend to perform the hand movements of FIG. 1, electrical signals can be detected. Electromyography (EMG) can be used to measure electrical activity that results from the contraction of extensor muscles 216, flexor muscles 218, extensor tendons 220, and flexor tendons 222. From this electrical activity, various hand movements and gestures shown in FIG. 1 can be detected and used to initiate or perform various functions.

The wrist is a common and socially acceptable location to house electronics (e.g., smart watches, fitness trackers), and muscles and tendons at this location can provide the electrical activity needed to detect hand movements and identify hand gestures being performed. However, it can be difficult to capture the necessary electrical signals, because wrist muscle mass can be low as compared to other areas of the forearm, and the wrist can change shape and produce numerous crevices as different hand movements are performed. In some examples, electrodes can be employed to address these challenges in a user-friendly form factor.

Figure 3A:
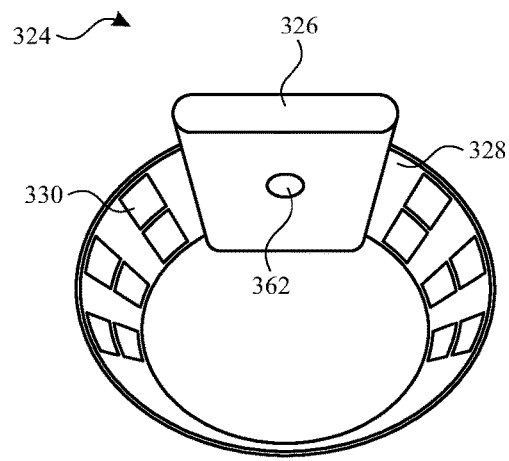
FIGS. 3A-3D illustrate example devices in which electrodes can be formed in a flexible band to detect hand movements and gestures according to some examples of the disclosure.
Figure 3B:
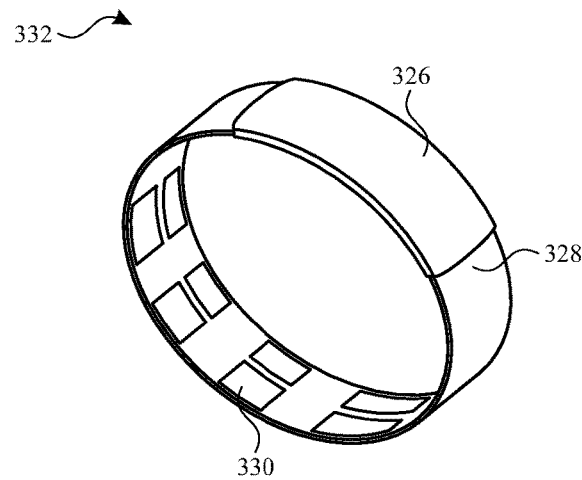
Figure 3C:
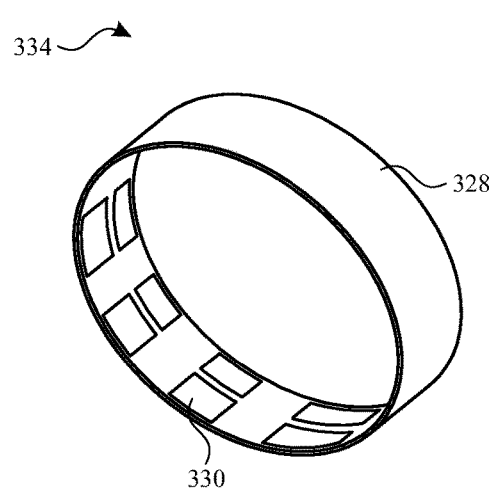
Figure 3D:
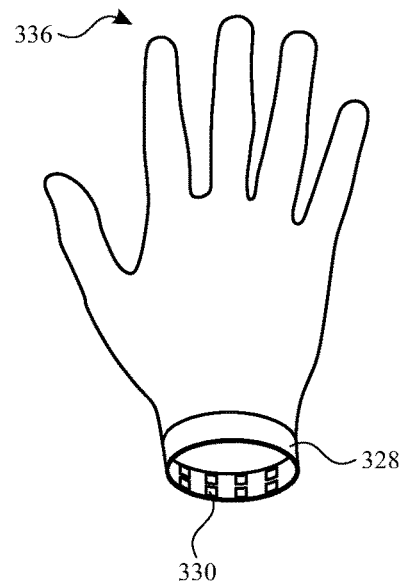

FIGS. 3A-3D illustrate example devices in which electrodes (textile and non-textile) can be formed in (e.g., woven, knitted, braided, embroidered, intertwined, fabricated, laminated, etc.) a flexible band to detect hand movements and gestures according to some examples of the disclosure. FIG. 3A illustrates an example smartwatch 324 having casing, housing or watch body 326 optionally including one or more electrodes 362, and flexible band or strap 328 including a plurality of electrodes 330. FIG. 3B illustrates an example activity or fitness tracker 332 having casing or housing 326 and flexible band or strap 328 including a plurality of electrodes 330. FIG. 3C illustrates an example fabric fashion accessory 334 having flexible band or strap 328 including a plurality of electrodes 330. In the example of FIG. 3C, one or more wireless communication modules (e.g., a Bluetooth Low Energy radio module, a Zigbee module) may be needed to facilitate transmission and/or reception of electrode signals to a separate device (e.g., a smartphone or other handheld or wearable device) for processing. FIG. 3D illustrates an example glove 336 (e.g., for AR/VR applications) having flexible cuff 328 including a plurality of electrodes 330. In the example of FIG. 3D, one or more wireless communication modules (e.g., a Bluetooth Low Energy radio module, a Zigbee module) may be needed to facilitate transmission and/or reception of electrode signals to a separate device (e.g., a smartphone or other handheld or wearable device) for processing.

Figure 4:
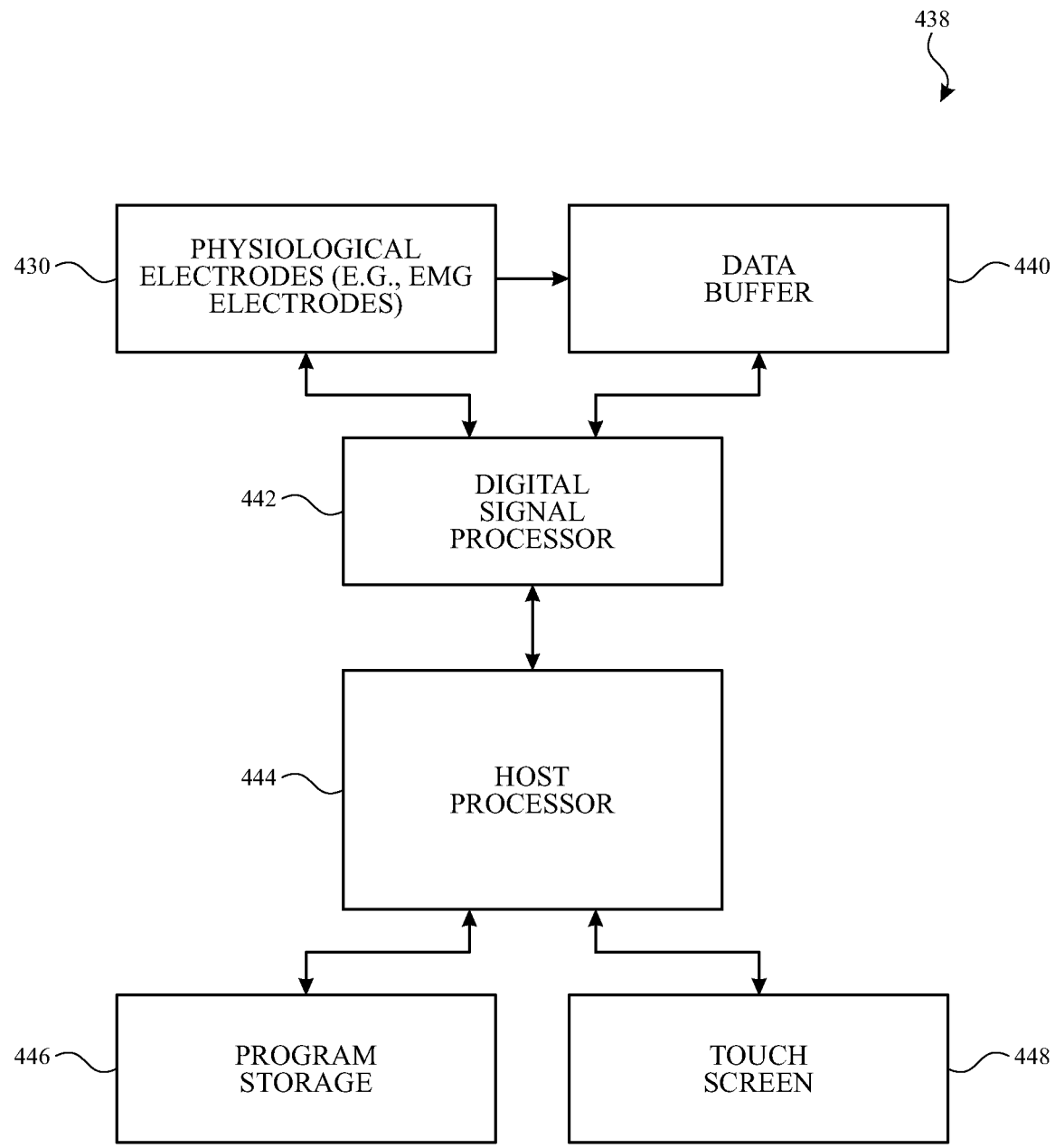
FIG. 4 illustrates a block diagram of an example computing system that illustrates one implementation of physiological signal capture and processing according to some examples of the disclosure.

FIG. 4 illustrates a block diagram of an example computing system 438 that illustrates one implementation of physiological signal capture and processing according to some examples of the disclosure. Portions of computing system 438 can be included in, for example, wearable devices 224 or 232 and/or any separate mobile or non-mobile, wearable or non-wearable computing device for physiological signal analysis and/or display. Computing system 438 can include one or more physiological electrodes 430 (e.g., EMG electrodes) to measure electrical signals (e.g., EMG signals) from a person contacting the EMG electrodes, data buffer 440 (or other volatile or non-volatile memory or storage) to store temporarily (or permanently) the physiological signals from the physiological electrodes 430, digital signal processor (DSP) 442 to analyze and process the physiological signals, host processor 444, program storage 446, and in some examples, touch screen 448 to perform display operations (e.g., to display real time EMG signals). In some examples, touch screen 448 may be replaced by a non-touch sensitive display.

Host processor 444 can be electrically coupled to program storage 446 to execute instructions stored in program storage 446 (e.g., a non-transitory computer-readable storage medium). Host processor 444 can, for example, provide control and data signals to generate a display image on touch screen 448, such as a display image of a user interface (UI). Host processor 444 can also receive outputs from DSP 442 (e.g., an EMG signal) and performing actions based on the outputs (e.g., display the EMG signal, play a sound, provide haptic feedback, etc.). Host processor 444 can also receive outputs (touch input) from touch screen 448 (or a touch controller, not-shown). The touch input can be used by computer programs stored in program storage 446 to perform actions that can include, but are not limited to, moving an object such as a cursor or pointer, scrolling or panning, adjusting control settings, opening a file or document, viewing a menu, making a selection, executing instructions, operating a peripheral device connected to the host device, answering a telephone call, placing a telephone call, terminating a telephone call, changing the volume or audio settings, storing information related to telephone communications such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, and/or the like. Host processor 444 can also perform additional functions that may not be related to touch processing and display.

Note that one or more of the functions described herein, including the processing of physiological signals, can be performed by firmware stored in memory (e.g., in DSP 442) and executed by one or more processors (in DSP 442), or stored in program storage 446 and executed by host processor 444. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

It is to be understood that the computing system 438 is not limited to the components and configuration of FIG. 4, but can include other or additional components (or omit components) in multiple configurations according to various examples. For example, an analog-to-digital converter (ADC) may be added between physiological electrodes 430 and DSP 442 to convert the signals to the digital domain, or touchscreen 448 can be omitted and the EMG signal or other information from the analysis and processing can be relayed to another device (e.g., a tablet, laptop, smartphone, computer, server, etc.) via wired or wireless connection that can include a display or other feedback mechanism for outputting a visual representation of the data or other notifications or information. Additionally, the components of computing system 438 can be included within a single device, or can be distributed between multiple devices.

Figure 5A:
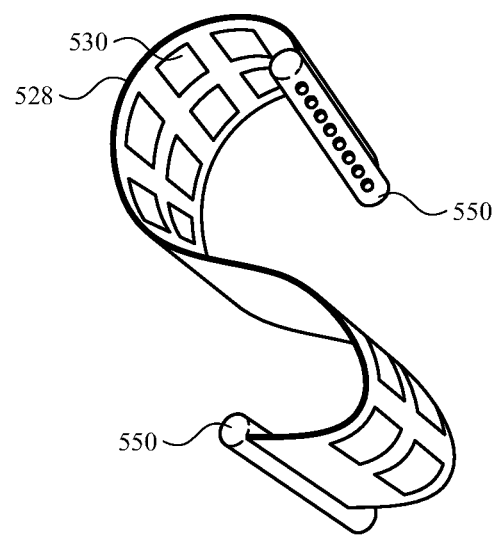
FIG. 5A illustrates an example flexible strap or band which has been separated from a housing according to some examples of the disclosure.

FIG. 5A illustrates an example flexible strap or band 528 which has been separated from a housing according to some examples of the disclosure. In the example of FIG. 5, strap or band 528 terminates in connectors 550, which is some examples are configured for slidable engagement with a housing. As mentioned above, electromyography (EMG) measures electrical activity that results from the contraction of muscles or other muscle activations. These electrical signals can be detected from on top of the skin through electrodes 530. EMG signal strength and quality can depend on where electrodes 530 are placed on the wrist or forearm, and can also depend on the contact between the electrodes and the skin. EMG signal strength can depend on where electrodes 530 are placed, because signals from muscles or tendons near the electrodes will be stronger than signals from muscles or tendons far from the electrodes. EMG signal quality can also depend on the quality of the contact between electrodes 530 and the user's skin, because reduced contact with the skin increases the impedance between the electrode and the skin, and may lower the signal to noise ratio (SNR) of the EMG signal.

Wet electrodes (those that include a conductive or electrolytic gel) can be impractical for removable wrist-based devices such as that shown in FIGS. 3A-3D. However, dry electrodes are rigid and are not able to conform to the curvature and crevices of the skin around the wrist, and it can be impractical to create a custom band with electrodes molded for a user's specific wrist size and shape, in particular because a user's wrist contours can change due to the activation of various muscles and tendons during the course of hand movements. Therefore, in some examples of the disclosure, electrodes 530 can be textile electrodes. Textile electrodes can be formed from conductive material such as conductive yarn or thread that is woven, knitted, braided, embroidered, or otherwise intertwined into non-conductive fabric. In other examples, electrodes 350 can be non-textile electrodes fabricated from conductive polymers (e.g., carbon composites) that are coated, printed or laminated onto non-conductive fabric. Electrodes that are formed in a stretchable piece of fabric can bend and stretch with the fabric itself, and conform to the contours of the wrist while maintaining user comfort and breathability. Because the electrodes in the fabric conform to the contours of a user's wrist during hand movement, signal errors due to severe displacement of the electrodes on the skin can be minimized.

Because of the variance in wrist sides, conventional wrist bands (e.g., watch bands) often use a buckle or a belt-like mechanism with notches, a clasp, or a hook-and-loop mechanism to allow users to adjust band length. However, this approach can compromise signal quality as it may change the number of electrodes in contact with the skin. Textile or non-textile electrodes formed in (e.g., woven, knitted, braided, embroidered, intertwined, fabricated, laminated, etc.) a stretchable band or strap 528 can overcome this problem as the band and electrodes can stretch to accommodate a certain amount of wrist size variation among users. In some examples, different sizes (e.g., small, medium, large, etc.) of a single stretchable band 528 with electrodes can be provided to accommodate different wrist sizes.

Figure 5B:
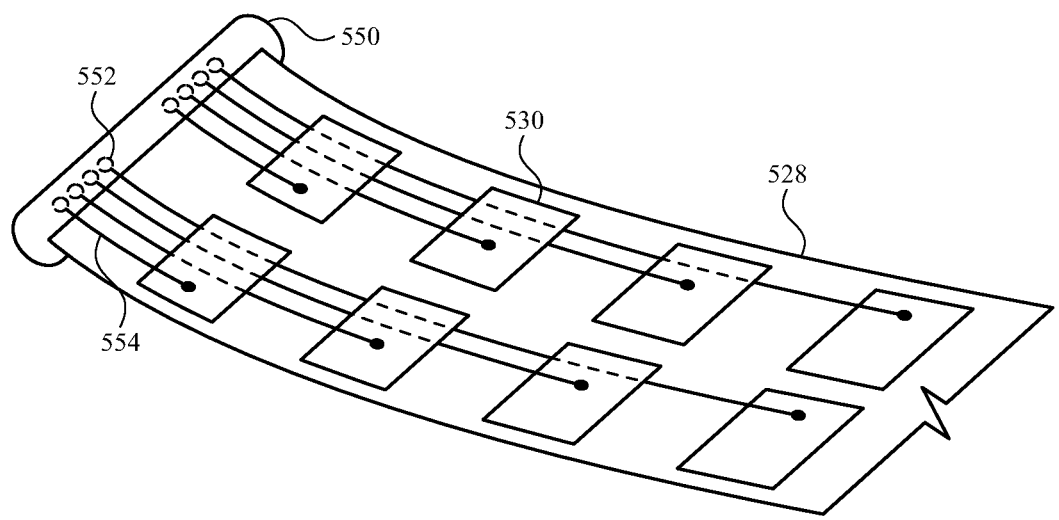
FIG. 5B illustrates a portion of a strap or band and the routing of electrodes to a connector according to some examples of the disclosure.

FIG. 5B illustrates a portion of strap or band 528 and the routing of electrodes 530 to connector 550 according to some examples of the disclosure. In the example of FIG. 5, each electrode 530 can be electrically coupled to metal contacts 552 on connector 550 via traces 554. In some examples, traces 554 can be silver thread, braided wires, or other conductive material that may contain an insulating coating. Although FIG. 5B illustrates traces 554 routed in straight lines, with some traces 554 passing under electrodes 530 (as indicated by dashed lines) without making electrical contact with the electrodes, other trace routing configurations can also be employed. For example, traces 554 can have bends or other strain-relief shapes such as serpentine or butterfly routing to allow the traces to flex without breaking when band 528 stretches and contracts. Furthermore, although FIG. 5B illustrates eight electrodes 530 in four rows and two columns routed to a single connector 550 on one end of band 528, in other examples any number of electrodes and any number of columns (including a single column) can be formed on the band and routed to connector 550. In other examples not shown in FIG. 5B, a second connector 550 at the other end of band 528 can also contain contacts 552 routed to other electrodes on the band. This configuration can reduce the length of traces 654 and reduce noise coupling.

FIG. 6A illustrates some details of contacts 652 in connector 650 according to some examples of the disclosure. In the example of FIG. 6A, connector 650 can be formed from rigid nonconductive material in an elongated shape such as a cylinder, though other shapes can also be utilized. Metal contacts 652 can be formed from conductive material on connector 650 in a generally concave shape, though other shapes can also be employed. Contacts 652 can be sized, shaped and located to make electrical contact with corresponding pogo pin contacts on a housing.

FIG. 6B illustrates some details of receptacle 656 in housing 626 for receiving connector 650 according to some examples of the disclosure. In the example of FIG. 6B, receptacle 656 can be formed within housing 626, and can be sized, shaped and located to allow connector 650 to slidably engage within the receptacle. Pogo pins 658 can be formed from electrically conductive material and located to engage with contacts 652 on connector 650. In some examples, pogo pins 658 can be dome-shaped and compressible within housing 626 to allow connector 650 and contacts 652 to slide within receptacle 656 and depress the pogo pins until they make electrical contact with the contacts.

FIGS. 6C-1 to 6C-3 illustrates the engagement of connector 650 of band 628 with housing 626 according to some examples of the disclosure. FIG. 6C-1 illustrates a front view of housing 626 with receptacle 656 and pogo pins 658 formed within the receptacle according to some examples of the disclosure. FIG. 6C-2 illustrates connector 650 of band 628 being slidably engaged with receptacle 656 of housing 626 according to examples of the disclosure. FIG. 6C-3 illustrates connector 650 fully engaged within housing 626 according to some examples of the disclosure. Once fully engaged, the electrodes on band 628 can be directly electrically coupled to circuitry within housing 626 via pogo pins 658. Although FIGS. 6A-6C illustrate contacts 652 on band 628 and pogo pins 658 on housing 626 in female/male configurations, respectively, in other examples the configurations can be reversed.

Figure 7:
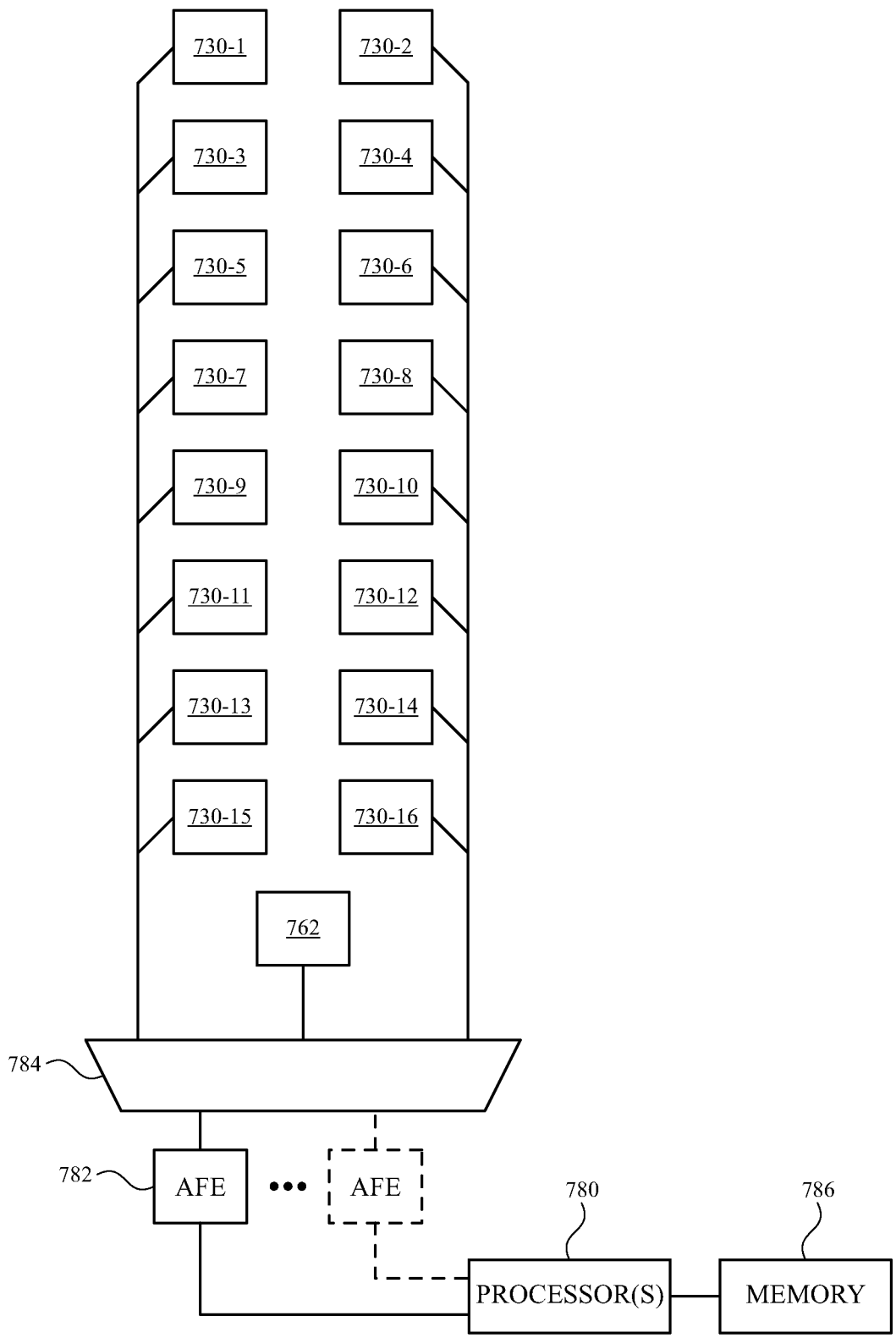
FIG. 7 illustrates a simplified schematic diagram of electrodes on a band, an electrode on a housing, a multiplexer block, one or more analog front end (AFE) circuits, one or more processors and a memory according to some examples of the disclosure.

FIG. 7 illustrates a simplified schematic diagram of electrodes 730, electrode 762, multiplexer block 784, one or more analog front end (AFE) circuits 782, one or more processors 780 and memory 786 according to some examples of the disclosure. In various examples, processor 780 can be a standalone processor, or it can be the same processor(s) shown in FIG. 4. Although FIG. 7 illustrates 16 electrodes 730-1 through 730-16 (located, for example, on the band of a device), any number of electrodes may be employed. In addition, although FIG. 7 illustrates eight horizontal rows of electrodes (with two electrodes in each row) in two vertical columns, other arrangements are possible. For example, four electrodes can be arranged in each row, in four vertical columns, and the number of rows can be different. Electrode 762 can represent an electrode on the housing of the device, and in some examples can be an existing electrode on a device housing that is also used for biometric sensing. Each of electrodes 730 and 762 can have a separate electrical coupling to multiplexer block 784. In some examples, multiplexer block 784 can include a plurality of multiplexers, each multiplexer dynamically configurable to electrically couple any one electrode 730 or electrode 762 to one input of one AFE 782. In some examples, multiplexer block 784 can be configured such that one AFE 782 can record a differential measurement of two electrodes (e.g., any two of electrodes 730 and electrode 762), and the result can be captured in memory 786 under control of processor 780. This process can be repeated with different electrodes at different times until the desired number of differential measurements of different combinations of electrodes have been captured. In other examples, multiple AFEs 782 can record differential measurements at about the same time (e.g., simultaneously), and the results can be captured in memory 786 under control of processor 780.

In some examples, unipolar measurements for any or all of electrodes 730 (acting as active electrodes) can be measured with respect to electrode 762 (acting as a reference electrode). However, in other examples, any one of electrodes 730 can act as the reference electrode, and electrode 762 and the other electrodes 730 can be active electrodes. Processor 780 can dynamically assign or designate any of electrodes 730 and electrode 762 as the active and reference electrodes when obtaining unipolar measurements. In the example of FIG. 7, up to 16 channels of unipolar data can be captured from different locations around the wrist. In some examples, unipolar measurements from active electrodes or the reference electrode whose amplitude is below a first threshold, whose signal-to-noise ratio (SNR) is below a second threshold, or that fails some other predetermined electrode contact criteria can be treated as an unreliable result from an unsatisfactory electrode contact, as determined by processor 780, and discarded. If fewer than all electrodes are being measured, the active electrode and/or the reference electrode with the unsatisfactory contact can be switched out via multiplexer block 784, and a different electrode can be designated as the active electrode or reference electrode and measured. In other examples, rather than activating a different electrode, the measurements from adjacent electrodes can be interpolated to compute an estimated measurement for the discarded electrode data. In some examples, multiplexer block 784 (under control of processor 780) can be configured to make electrode 762 or any one of electrodes 730 the reference electrode, in the event that the reference electrode itself has a bad contact.

In some examples, bipolar measurements from pairs of electrodes can be captured. Bipolar measurements capture voltage differences between pairs of electrodes, and do not require a specific reference electrode. The bipolar measurement of a pair of electrodes in a single row (e.g., electrodes 730-3 and 730-4 in the second row) can be obtained by electrically coupling one of the electrodes in the pair (which can act as the active electrode) to one of the inputs of a differential amplifier, and electrically coupling the other electrode in the pair (which can act as the reference electrode) to the other input of the differential amplifier. The output of the differential amplifier can be considered the bipolar measurement from the electrode pair, representing one channel of data. Similarly, the bipolar measurement of another pair of electrodes in different row (e.g., electrodes 730-7 and 730-8 in the fourth row) can be obtained to generate another channel of data. Multiple bipolar measurements from different electrode pairs can be analyzed to determine various hand movements and gestures. Processor 780 can dynamically assign or designate any of electrodes 730 and electrode 762 as active and reference electrode pairs when obtaining bipolar measurements, although the electrode pairs are most often close to each other, such as in the same row. In the example of FIG. 7, bipolar measurements from electrode pairs in the same row (e.g., electrodes 730-1 and 730-2, electrodes 730-3 and 730-4, etc.) can be recorded, resulting in up to eight channels of data being captured from different locations around the wrist. Optionally, a ninth channel of data can be captured if electrode 762 is paired with a neighboring electrode. Bipolar measurements on a subset of rows of electrodes (e.g., less than all rows of electrodes), optionally captured less frequently (e.g., with a lower sampling rate), can be used in lower power use cases where high accuracy is not critical, and communication, amplifier and processing activities can be reduced to lower power consumption. This lower power and lower granularity gesture recognition mode could be used to trigger a wakeup to allow for a higher power and higher fidelity gesture recognition state using unipolar measurements and increasing the sampling rate and the number of active electrodes measured. For example, processor 780 can determine that the device is in a low power state, or can place the device in a low power state, where bipolar measurements on only two pairs of electrodes (e.g., electrodes 730-3 and 730-4 as one pair, and electrodes 730-11 and 730-12 as a second pair, as designated by processor 780) can be obtained, and the measurements can be obtained with a lower sampling rate (as compared to a higher power mode). When these measurements are processed and determined to represent an "activate" gesture (e.g., a particular hand gesture intended to trigger more comprehensive hand gesture detection), the device (under control of processor 780) can switch to a higher bandwidth gesture sensing mode (e.g., a unipolar measurement mode) where measurements are obtained for more electrodes (as determined by the processor), and more frequently than in the lower power mode. Alternatively, the higher power state can be activated by inputs, interrupts and triggers other than hand gestures.

In some examples, bipolar measurements from electrode pairs whose amplitude is below (or above) a first threshold, whose signal-to-noise ratio (SNR) is below a second threshold, or that fails some other predetermined electrode contact criteria can be treated as an unreliable result from an unsatisfactory electrode contact and discarded. If fewer than all electrode pairs are being measured, the electrode pair with the unsatisfactory contact can be switched out via multiplexer block 784 and a previously unmeasured electrode pair can be recorded. In other words, one channel of unsatisfactory bipolar data can be replaced with another channel of bipolar data. In other examples, rather than activating a different electrode pair, the measurements from adjacent electrode pairs can be interpolated to compute an estimated measurement for the discarded electrode data.

In some examples, electrodes 730 can be located relatively uniformly across the band into which they are formed (e.g., woven, knitted, fabricated, intertwined, etc.). Uniform electrode coverage around the wrist can allow electrode measurements to be recorded from most or all of the extensor and flexor muscles with tendon endings at the wrist, which can enable a wide range of gesture detection and classification. Hand movement "signatures" comprised of various expected electrode measurements at various locations at certain times can be stored or determined, either empirically during product development or as a result of the device being "trained" after the user performs a requested series of hand movements, as controlled by processor 780. During actual user hand movement, unipolar or bipolar measurements can be captured over a period of time at electrodes 730 and 762 and compared by processor 780 to the known hand movement "signatures." If the captured data matches a particular hand movement "signature" or a series of signatures, a hand movement or gesture can be identified by processor 780. The number of electrode measurements to be taken can depend on a mode of operation. For example, if only coarse gesture recognition is needed (e.g., only a fist gesture, an open hand gesture, and a pinch gesture need to be detected), only three or four pairs of electrodes 730, located at the top and bottom of the wrist, may need to be monitored to generate three or four channels of bipolar data to detect flexor and extensor activity that matches the signatures for those gestures. However, if the detection of more gestures, and/or more complex gestures is desired, then additional electrodes may need to be monitored.

Because of the flexibility offered by multiplexer block 784, the choices between (1) unipolar and bipolar measurements, (2) which electrodes 730 and 762 (and how many) are going to be the active electrodes and which electrode is going to be reference electrode in unipolar measurements, and (3) which electrodes are going to be paired together (and how many pairs are going to be utilized) in bipolar measurements, can be performed in software. Electrodes 730 could also be used for recording other modalities, like the galvanic skin response (which measures perspiration on the skin by measuring differences in conductivity of the skin across time) or electrocardiograms (ECG).

Figure 8:
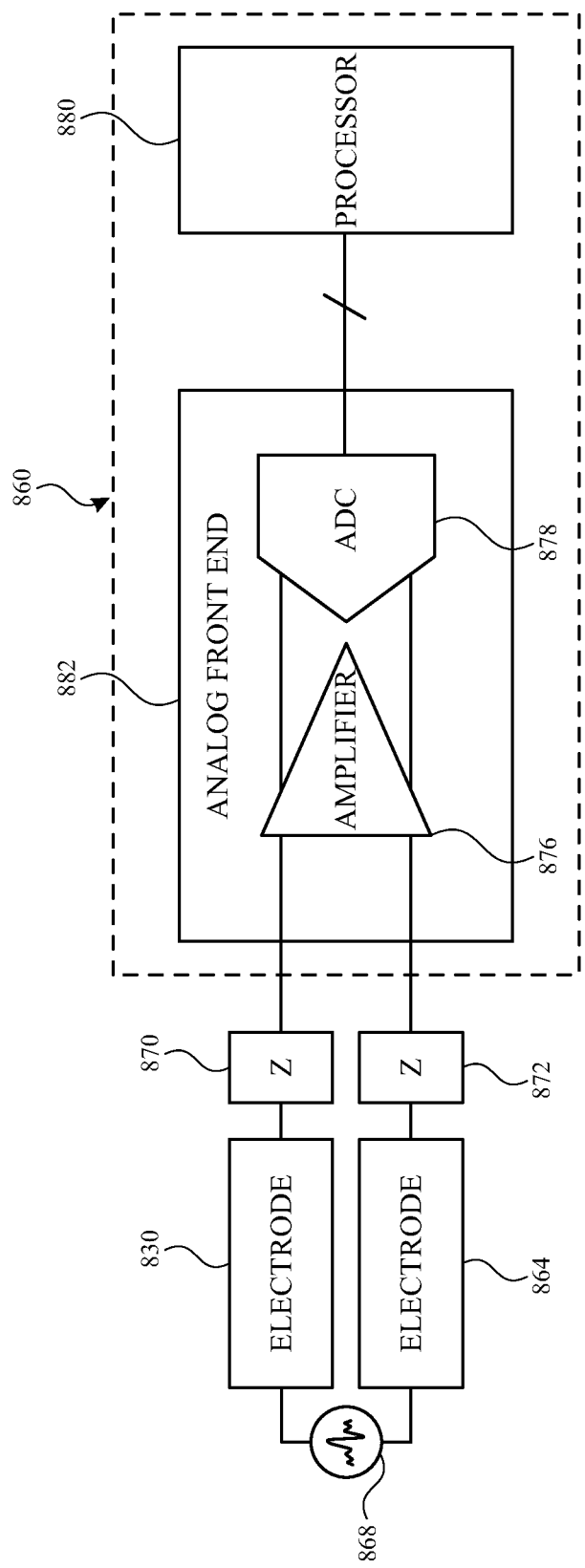
FIG. 8 illustrates two representative electrodes and simplifier circuitry of a device for measuring physiological signals according to examples of the disclosure.

FIG. 8 illustrates two representative electrodes and simplified circuitry of a device for measuring physiological signals according to examples of the disclosure. In FIG. 8, differential measurement circuitry 860 can be located in a housing of the device and can include processor 880 and analog front end 882. Although the simplified measurement circuitry of FIG. 8 can measure signals from two electrodes, it should be understood that one or a plurality of measurement circuits shown in FIG. 8 can be employed and multiplexed so that all of the electrodes on the band can be measured in a sequence of measurements, or depending on the number of measurement circuits, all electrodes can be measured simultaneously. Note that multiplexer circuitry found in the multiplexer block of FIG. 7 is not shown in differential measurement circuitry 860 of FIG. 8 for purposes of simplifying the figure. Electrode 830 and electrode 864 can be located either on a band or the housing of the device. In unipolar measurements, different electrodes 830 are typically differentially measured with respect to the same electrode 864, which acts as the reference electrode. In bipolar measurements, electrode 830 and electrode 864 are different pairs of electrodes, often in the same row. In some examples, analog front end 882 includes amplifier 876 and analog-to-digital converter (ADC) 878. Electromyography (EMG) is the recording of electrical potential generated by muscles and tendons when activated by the peripheral nervous system of the body. EMG can detect muscle and tendon activity, but are relatively low amplitude signals as compared to ECG signals, so EMG signals can be measured using "referential" measurements. In unipolar measurements, each referential measurement is a differential measurement of the electrical activity between an active electrode (e.g., an electrode on the band of the device) and a reference electrode (e.g., an electrode on the housing of the device) as described with respect to FIG. 7 above. For example, one reference electrode can be used to perform differential measurements with respect to all other active electrodes. In bipolar measurements, each referential measurement is a differential measurement of the electrical activity between a pair of electrodes (one acting as an active electrode and the other acting as a reference electrode) as described with respect to FIG. 7 above. Amplifier 876 can be a differential amplifier electrically coupled to electrode 830 (e.g., on the inverting input or on the non-inverting input) and to electrode 864 (e.g., on the non-inverting input or on the inverting input). Networks 870 and 872 represent the equivalent circuits of the signal paths between electrode 830 and amplifier 876, or between electrode 864 and the amplifier 876, respectively. In some examples, networks 870 and 872 can include circuit components (e.g., resistors, capacitors, inductors and/or diodes) and/or can include impedances inherent in the signal paths (e.g., routing impedances, parasitic impedances, etc.). In some examples, networks 870 and 872 can provide electrostatic discharge (ESD) protection for differential measurement circuitry 860 and/or provide safety by limiting or preventing electrical currents being applied to the user's skin and/or preventing unexpected or unintentional external signals from entering the device and causing damage. In some examples, amplifier 876 can output an amplified differential signal and ADC 878 can convert the amplified differential signal into a digital signal. In some examples, amplifier 876 can output an amplified single-ended output. In some examples, the output of ADC 878 can be a multi-bit signal (e.g., 8 bits, 12 bits, 24 bits, etc.) electrically coupled to processor 880. The multi-bit signal can be transmitted from analog front end 882 to processor 880 serially or in parallel. In some examples, ADC 878 can be a differential ADC and convert a differential analog input to a digital output. In some examples, ADC 878 can be single-ended and convert a single-ended analog input to a digital output. In some examples, differential amplifier 876 can be implemented with two single-ended amplifiers and ADC 878 can be implemented with two ADCs (each electrically coupled to the output of one of the single-ended amplifiers).

As described above, electrode 830 and electrode 864 can make contact with the wrist of the user. When electrode 830 and electrode 864 make contact with a user's wrist, the electrodes can receive a physiological signal from the user. In FIG. 8, the user is represented as physiological signal source 868. In some examples, when the user touches electrode 830, a path can be created through physiological signal source 868 from electrode 830 to electrode 864. In some examples, contacting electrode 830 can cause differential measurement circuitry 860 to measure a physiological signal from physiological signal source 868.

Figure 9:
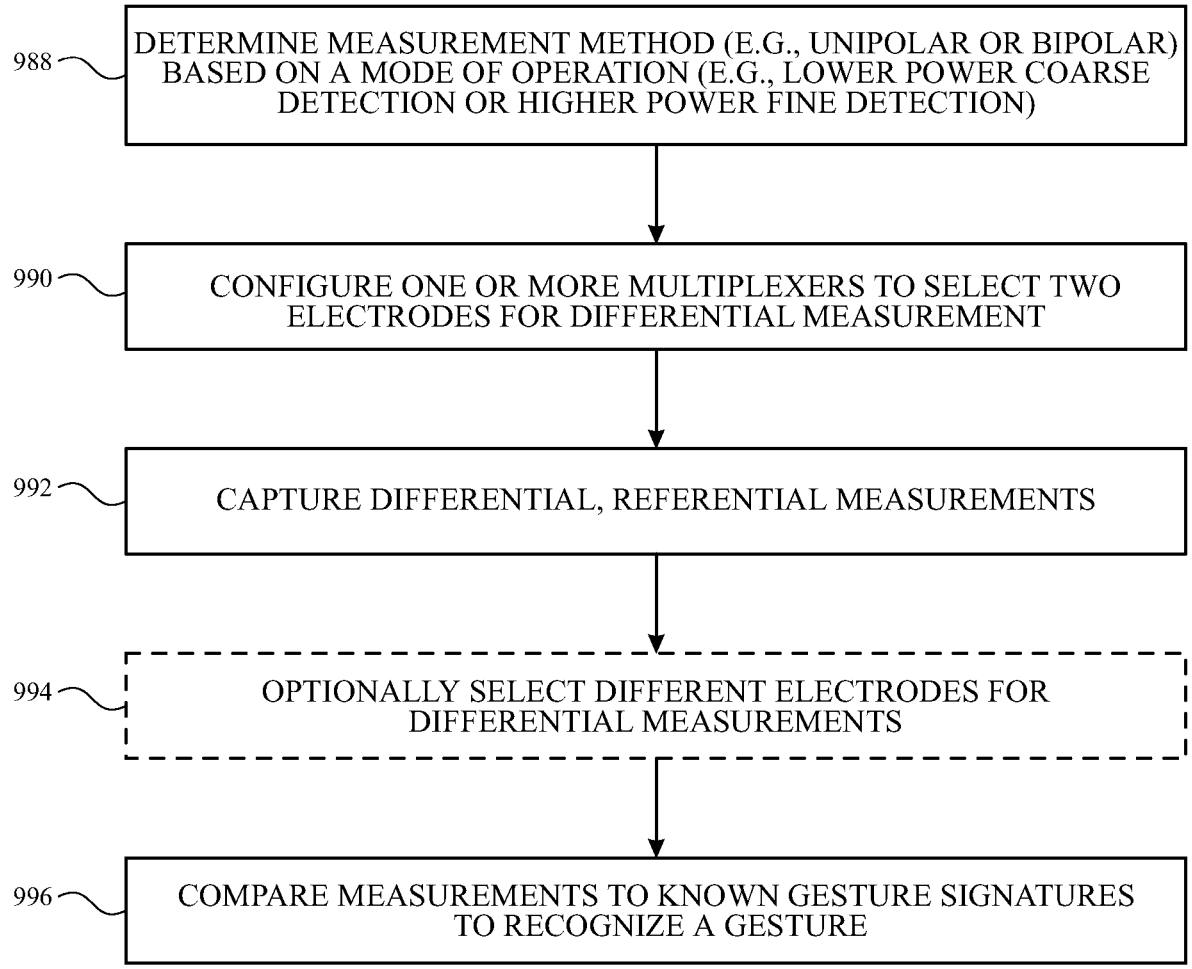
FIG. 9 illustrates a flow diagram illustrating the use of electrodes for gesture recognition according to some examples of the disclosure.

FIG. 9 illustrates a flow diagram illustrating the use of electrodes for gesture recognition according to some examples of the disclosure. In the example of FIG. 9, a measurement method (e.g., unipolar or bipolar) based on a mode of operation (e.g., lower power coarse detection or higher power fine detection) can be determined at 988. In accordance with the determined measurement method and mode of operation, one or more multiplexers can be configured to select two electrodes for differential measurement at 990. This differential measurement of two electrodes can be performed multiple times (e.g., up to nine pairs of electrodes in bipolar mode or 17 total electrodes in unipolar mode, in the example configuration of FIG. 7). Differential, referential measurements of the two electrodes can be captured at 992. Optionally, the one or more multiplexers can be reconfigured to select different electrodes for differential measurement at 994. After satisfactory measurements are obtained, they can be compared against known gesture signatures to recognize a gesture being performed at 996.

Therefore, according to the above, some examples of the disclosure are directed to a device for gesture recognition, comprising a wearable band, a housing including one or more multiplexers and one or more differential measurement circuits communicatively coupled to the one or more multiplexers and configured for making referential measurements, and a plurality of electrodes located on one or both of the wearable band and the housing, wherein the one or more multiplexers are dynamically configurable to electrically couple different pairs of electrodes of the plurality of electrodes to one of the differential measurement circuits to obtain a referential measurement for recognizing a gesture. Additionally or alternatively to one or more of the examples disclosed above, in some examples the housing further includes one or more processors communicatively coupled to the one or more differential measurement circuits, the one or more processors configured to receive referential measurements from the one or more differential measurement circuits, identify one or more hand movements from the referential measurements, and recognize one or more gestures from the identified one or more hand movements. Additionally or alternatively to one or more of the examples disclosed above, in some examples the device further comprises one or more processors communicatively coupled to the one or more differential measurement circuits and the one or more multiplexers, the one or more processors configured to designate a first electrode of the plurality of electrodes as a reference electrode, designate one or more second electrodes of the plurality of electrodes as active electrodes, and configure the one or more multiplexers to electrically couple the reference electrode and one of the active electrodes to one of the differential measurement circuits to obtain a unipolar measurement. Additionally or alternatively to one or more of the examples disclosed above, in some examples the one or more processors are further configured to receive a first referential measurement from a first differential measurement circuit of the one or more differential measurement circuits, determine if the first referential measurement satisfies an electrode contact criterion, in accordance with a determination that the first referential measurement satisfies the electrode contact criterion, process the first referential measurement, and in accordance with a determination that the first referential measurement does not satisfy the electrode contact criterion, configure the one or more multiplexers to couple a different active electrode to the first differential measurement circuit. Additionally or alternatively to one or more of the examples disclosed above, in some examples the one or more processors are further configured to receive a first referential measurement from a first differential measurement circuit of the one or more differential measurement circuits, determine if the first referential measurement satisfies an electrode contact criterion, in accordance with a determination that the first referential measurement satisfies the electrode contact criterion, process the first referential measurement, and in accordance with a determination that the first referential measurement does not satisfy the electrode contact criterion, designate a third electrode of the plurality of electrodes as the reference electrode, and configure the one or more multiplexers to electrically couple the third electrode to the first differential measurement circuit. Additionally or alternatively to one or more of the examples disclosed above, in some examples the one or more processors are further configured to determine a power state of the device, in accordance with a determination that the device is in a low power state, designate a first subset of the one or more second electrodes as the active electrodes. Additionally or alternatively to one or more of the examples disclosed above, in some examples the one or more processors are further configured to detect an activation event, and in accordance with the detection of the activation event, change the power state of the device to a high power state, and designate a second subset of the one or more second electrodes as the active electrodes, wherein the second subset is larger than the first subset. Additionally or alternatively to one or more of the examples disclosed above, in some examples the one or more processors are further configured to dynamically configure the one or more multiplexers to electrically couple one or more of the active electrodes to one or more of the differential measurement circuits at different times to obtain unipolar measurements from the one or more active electrodes. Additionally or alternatively to one or more of the examples disclosed above, in some examples the one or more processors are further configured to dynamically configure the one or more multiplexers to electrically couple a plurality of the active electrodes to a plurality of the differential measurement circuits at the same time to obtain simultaneous unipolar measurements from the plurality of active electrodes. Additionally or alternatively to one or more of the examples disclosed above, in some examples the reference electrode is located on the housing of the device. Additionally or alternatively to one or more of the examples disclosed above, in some examples the device further comprises one or more processors communicatively coupled to the one or more differential measurement circuits and the one or more multiplexers, the one or more processors configured to group the plurality of electrodes into a plurality of electrode pairs; and configure the one or more multiplexers to obtain bipolar measurements by electrically coupling the electrodes in one or more of the plurality of electrode pairs to the one or more differential measurement circuits. Additionally or alternatively to one or more of the examples disclosed above, in some examples the one or more processors are further configured to receive a bipolar measurement from an electrode pair coupled to one of the differential measurement circuits, determine if the bipolar measurement satisfies an electrode contact criterion, in accordance with a determination that the bipolar measurement satisfies the electrode contact criterion, process the bipolar measurement, and in accordance with a determination that the bipolar measurement does not satisfy the electrode contact criterion, configure the one or more multiplexers to couple a different electrode pair to the differential measurement circuit. Additionally or alternatively to one or more of the examples disclosed above, in some examples the one or more processors are further configured to determine a power state of the device, and in accordance with a determination that the device is in a low power state, electrically couple a first subset of the plurality of electrode pairs to the one or more differential measurement circuits. Additionally or alternatively to one or more of the examples disclosed above, in some examples the one or more processors are further configured to detect an activation event, and in accordance with the detection of the activation event, change the power state of the device to a high power state, and electrically couple a second subset of the plurality of electrode pairs to the one or more differential measurement circuits, wherein the second subset is larger than the first subset. Additionally or alternatively to one or more of the examples disclosed above, in some examples the one or more processors are further configured to dynamically configure the one or more multiplexers to electrically couple at least some of the plurality of electrode pairs to one or more of the differential measurement circuits at different times to obtain bipolar measurements from the plurality of electrode pairs. Additionally or alternatively to one or more of the examples disclosed above, in some examples the one or more processors are further configured to dynamically configure the one or more multiplexers to electrically couple at least some of the plurality of the electrode pairs to a plurality of the differential measurement circuits at the same time to obtain simultaneous unipolar measurements from the plurality of electrode pairs. Additionally or alternatively to one or more of the examples disclosed above, in some examples the device further comprises one or more processors communicatively coupled to the one or more differential measurement circuits and the one or more multiplexers, the one or more processors configured to dynamically switch between unipolar and bipolar modes of operation, wherein in the unipolar mode of operation, for each of a plurality of unipolar measurements the one or more processors are further configured to electrically couple an active electrode and a reference electrode to one of the differential measurement circuits, and wherein in the bipolar mode of operation, the one or more processors are further configured to electrically couple each of a plurality of electrode pairs to one of the differential measurement circuits. Additionally or alternatively to one or more of the examples disclosed above, in some examples a first subset of the plurality of electrodes are textile electrodes located on the wearable band. Additionally or alternatively to one or more of the examples disclosed above, in some examples the wearable band is a flexible band. Additionally or alternatively to one or more of the examples disclosed above, in some examples the wearable band further comprises electrical conductors configured for electrically coupling the plurality of electrodes to the one or more multiplexers, the electrical conductors shaped for providing strain relief. Additionally or alternatively to one or more of the examples disclosed above, in some examples the housing is wearable and mechanically coupled to the wearable band. Additionally or alternatively to one or more of the examples disclosed above, in some examples the device further comprises a connector assembly configured for providing electrical connections between the wearable band and the housing, the connector assembly comprising a first connector attached to the wearable band and including a plurality of first contacts electrically connected to at least some of the plurality of electrodes, and a second connector attached to the housing and including a plurality of second contacts electrically coupled to the at least one multiplexer, wherein at least one of the plurality of first contacts and the plurality of second contacts includes one or more pogo pins.

Some examples of the disclosure are directed to a method for gesture recognition, comprising electrically coupling one or more pairs of electrodes of a plurality of electrodes to one or more differential measurement circuits, wherein at least some of the plurality of electrodes are formed on a wearable band, receiving referential measurements from the one or more differential measurement circuits, identifying one or more hand movements from the referential measurements, and recognizing one or more gestures from the identified one or more hand movements. Additionally or alternatively to one or more of the examples disclosed above, in some examples the method further comprises designating a first electrode of the plurality of electrodes as a reference electrode, designating one or more second electrodes of the plurality of electrodes as active electrodes, and electrically coupling the reference electrode and one of the active electrodes to one of the differential measurement circuits to obtain a unipolar measurement. Additionally or alternatively to one or more of the examples disclosed above, in some examples the method further comprises receiving a first referential measurement from a first differential measurement circuit of the one or more differential measurement circuits, determining if the first referential measurement satisfies an electrode contact criterion, in accordance with a determination that the first referential measurement satisfies the electrode contact criterion, processing the first referential measurement, and in accordance with a determination that the first referential measurement does not satisfy the electrode contact criterion, electrically coupling a different active electrode to the first differential measurement circuit. Additionally or alternatively to one or more of the examples disclosed above, in some examples the method further comprises receiving a first referential measurement from a first differential measurement circuit of the one or more differential measurement circuits, determining if the first referential measurement satisfies an electrode contact criterion, in accordance with a determination that the first referential measurement satisfies the electrode contact criterion, processing the first referential measurement, and in accordance with a determination that the first referential measurement does not satisfy the electrode contact criterion, designating a third electrode of the plurality of electrodes as the reference electrode, and electrically coupling the third electrode to the first differential measurement circuit. Additionally or alternatively to one or more of the examples disclosed above, in some examples the method further comprises determining a power state of the device, and in accordance with a determination that the device is in a low power state, designating a first subset of the one or more second electrodes as the active electrodes. Additionally or alternatively to one or more of the examples disclosed above, in some examples the method further comprises detecting an activation event, and in accordance with the detection of the activation event, changing the power state of the device to a high power state, and designating a second subset of the one or more second electrodes as the active electrodes, wherein the second subset is larger than the first subset. Additionally or alternatively to one or more of the examples disclosed above, in some examples the method further comprises electrically coupling one or more of the active electrodes to one or more of the differential measurement circuits at different times to obtain unipolar measurements from the one or more active electrodes. Additionally or alternatively to one or more of the examples disclosed above, in some examples the method further comprises electrically coupling a plurality of the active electrodes to a plurality of the differential measurement circuits at the same time to obtain simultaneous unipolar measurements from the plurality of active electrodes. Additionally or alternatively to one or more of the examples disclosed above, in some examples the method further comprises grouping the plurality of electrodes into a plurality of electrode pairs, and obtaining bipolar measurements by electrically coupling the electrodes in one or more of the plurality of electrode pairs to the one or more differential measurement circuits. Additionally or alternatively to one or more of the examples disclosed above, in some examples the method further comprises receiving a bipolar measurement from an electrode pair coupled to one of the differential measurement circuits, determining if the bipolar measurement satisfies an electrode contact criterion, in accordance with a determination that the first referential measurement satisfies the electrode contact criterion, processing the bipolar measurement, and in accordance with a determination that the bipolar measurement does not satisfy the electrode contact criterion, electrically coupling a different electrode pair to the differential measurement circuits. Additionally or alternatively to one or more of the examples disclosed above, in some examples the method further comprises determining a power state of the device, and in accordance with a determination that the device is in a low power state, electrically couple a first subset of the plurality of electrode pairs to the one or more differential measurement circuits. Additionally or alternatively to one or more of the examples disclosed above, in some examples the method further comprises detecting an activation event, and in accordance with the detection of the activation event, changing the power state of the device to a high power state, and electrically coupling a second subset of the plurality of electrode pairs to the one or more differential measurement circuits, wherein the second subset is larger than the first subset. Additionally or alternatively to one or more of the examples disclosed above, in some examples the method further comprises electrically coupling at least some of the plurality of electrode pairs to one or more of the differential measurement circuits at different times to obtain bipolar measurements from the plurality of electrode pairs. Additionally or alternatively to one or more of the examples disclosed above, in some examples the method further comprises electrically coupling at least some of the plurality of electrode pairs to a plurality of the differential measurement circuits at the same time to obtain simultaneous unipolar measurements from the plurality of electrode pairs. Additionally or alternatively to one or more of the examples disclosed above, in some examples the method further comprises dynamically switching between unipolar and bipolar modes of operation, wherein in the unipolar mode of operation, the method further comprises, for each of a plurality of unipolar measurements, electrically coupling an active electrode and a reference electrode to one of the differential measurement circuits, and wherein in the bipolar mode of operation, the method further comprises electrically coupling each of a plurality of electrode pairs to one of the differential measurement circuits.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:
1. A device for gesture recognition, comprising:
  a wearable band;
  a housing including
    one or more multiplexers, and
    one or more differential measurement circuits communicatively coupled to the one or more multiplexers and configured for making referential measurements;
  a plurality of electrodes located on one or both of the wearable band and the housing; and
  one or more processors communicatively coupled to the one or more differential measurement circuits and the one or more multiplexers, the one or more processors programmed to
    configure the one or more multiplexers to electrically couple one or more different pairs of electrodes of the plurality of electrodes to one of the differential measurement circuits,
    obtain a referential measurement from the differential measurement circuit,
    determine if the referential measurement satisfies an electrode contact criterion,
    in accordance with a determination that the referential measurement satisfies the electrode contact criterion, process the referential measurement, and
    in accordance with a determination that the referential measurement does not satisfy the electrode contact criterion, configure the one or more multiplexers to couple a different electrode pair to the differential measurement circuit.

2. The device of claim 1, the one or more processors further programmed to:
identify one or more hand movements from the processed referential measurement; and
recognize one or more gestures from the identified one or more hand movements.

3. The device of claim 1, the one or more processors further programmed to:
designate a first electrode of the plurality of electrodes as a reference electrode;
designate one or more second electrodes of the plurality of electrodes as active electrodes; and
configure the one or more multiplexers to electrically couple the reference electrode and one of the active electrodes to one of the differential measurement circuits to obtain a unipolar measurement.

4. The device of claim 3, the one or more processors further programmed to:
in accordance with a determination that the referential measurement does not satisfy the electrode contact criterion, configure the one or more multiplexers to couple a different active electrode to the differential measurement circuit.

5. The device of claim 3, the one or more processors further programmed to:
in accordance with a determination that the referential measurement does not satisfy the electrode contact criterion, designate a third electrode of the plurality of electrodes as the reference electrode, and configure the one or more multiplexers to electrically couple the third electrode to the differential measurement circuit.

6. The device of claim 3, the one or more processors further programmed to:
determine a power state of the device; and
in accordance with a determination that the device is in a low power state, designate a first subset of the one or more second electrodes as the active electrodes.

7. The device of claim 6, the one or more processors further programmed to:
detect an activation event; and
in accordance with the detection of the activation event, change the power state of the device to a high power state, and designate a second subset of the one or more second electrodes as the active electrodes;
wherein the second subset is larger than the first subset.

8. The device of claim 3, the one or more processors further programmed to dynamically configure the one or more multiplexers to electrically couple one or more of the active electrodes to one or more of the differential measurement circuits at different times to obtain unipolar measurements from the one or more active electrodes.

9. The device of claim 1, the one or more processors programmed to:
group the plurality of electrodes into a plurality of electrode pairs; and
configure the one or more multiplexers to obtain bipolar measurements by
electrically coupling the electrodes in one or more of the plurality of electrode pairs to the one or more differential measurement circuits.

10. The device of claim 9, the one or more processors further programmed to:
receive a bipolar measurement from an electrode pair coupled to one of the differential measurement circuits;
determine if the bipolar measurement satisfies an electrode contact criterion;
in accordance with a determination that the bipolar measurement satisfies the electrode contact criterion, process the bipolar measurement; and
in accordance with a determination that the bipolar measurement does not satisfy the electrode contact criterion, configure the one or more multiplexers to couple a different electrode pair to the differential measurement circuit.

11. The device of claim 9, the one or more processors further programmed to:
determine a power state of the device; and
in accordance with a determination that the device is in a low power state, electrically couple a first subset of the plurality of electrode pairs to the one or more differential measurement circuits.

12. The device of claim 9, the one or more processors further programmed to dynamically configure the one or more multiplexers to electrically couple at least some of the plurality of electrode pairs to a plurality of the differential measurement circuits at a same time to obtain simultaneous unipolar measurements from the plurality of electrode pairs.

13. The device of claim 1, the one or more processors programmed to:
dynamically switch between unipolar and bipolar modes of operation;
wherein in the unipolar mode of operation, for each of a plurality of unipolar measurements, electrically couple an active electrode and a reference electrode to one of the differential measurement circuits; and
wherein in the bipolar mode of operation, electrically couple each of a plurality of electrode pairs to one of the differential measurement circuits.

14. The device of claim 2, further comprising a connector assembly configured for providing electrical connections between the wearable band and the housing, the connector assembly comprising:
a first connector attached to the wearable band and including a plurality of first contacts electrically connected to at least some of the plurality of electrodes; and
a second connector attached to the housing and including a plurality of second contacts electrically coupled to at least one multiplexer of the one or more multiplexers;
wherein at least one of the plurality of first contacts and the plurality of second contacts includes one or more pogo pins.

15. A method for gesture recognition, comprising:
electrically coupling one or more pairs of electrodes of a plurality of electrodes to one or more differential measurement circuits, wherein at least some of the plurality of electrodes are formed on a wearable band disposed on a device for gesture recognition;
receiving one or more referential measurements from the one or more differential measurement circuits, including one referential measurement for each of the electrically coupled one or more pairs of electrodes;
determining if the one or more referential measurements satisfy an electrode contact criterion;
in accordance with a determination that the one or more referential measurements satisfy the electrode contact criterion,
processing the one or more referential measurements, identifying one or more hand movements from the one or more referential measurements, and recognizing one or more gestures from the identified one or more hand movements; and in accordance with a determination that a first referential measurement from a first differential measurement circuit does not satisfy the electrode contact criterion, configuring one or more multiplexers to couple an electrode pair different from the electrode pair associated with the first referential measurement to the first differential measurement circuit.

16. The method of claim 15, further comprising:
designating a first electrode of the plurality of electrodes as a reference electrode;
designating one or more second electrodes of the plurality of electrodes as active electrodes; and
electrically coupling the reference electrode and one of the active electrodes to one of the differential measurement circuits to obtain a unipolar measurement.

17. The method of claim 16, further comprising:
in accordance with a determination that the first referential measurement does not satisfy the electrode contact criterion, electrically coupling a different active electrode to the first differential measurement circuit.

18. The method of claim 16, further comprising:
in accordance with a determination that the first referential measurement does not satisfy the electrode contact criterion, designating a third electrode of the plurality of electrodes as the reference electrode, and electrically coupling the third electrode to the first differential measurement circuit.

19. The method of claim 16, further comprising electrically coupling one or more of the active electrodes to one or more of the differential measurement circuits at different times to obtain unipolar measurements from the one or more active electrodes.

20. The method of claim 15, further comprising:
grouping the plurality of electrodes into a plurality of electrode pairs; and
obtaining bipolar measurements by
electrically coupling the electrodes in one or more of the plurality of electrode pairs to the one or more differential measurement circuits.

21. The method of claim 20, further comprising:
receiving a bipolar measurement from an electrode pair coupled to one of the differential measurement circuits;
determining if the bipolar measurement satisfies an electrode contact criterion;
in accordance with a determination that the bipolar measurement satisfies the electrode contact criterion, processing the bipolar measurement; and
in accordance with a determination that the bipolar measurement does not satisfy the electrode contact criterion, electrically coupling a different electrode pair to the differential measurement circuits.

22. The method of claim 20, further comprising:
determining a power state of the device; and
in accordance with a determination that the device is in a low power state, electrically couple a first subset of the plurality of electrode pairs to the one or more differential measurement circuits.

23. The method of claim 22, further comprising:
detecting an activation event; and
in accordance with the detection of the activation event, changing the power state of the device to a high power state, and electrically coupling a second subset of the plurality of electrode pairs to the one or more differential measurement circuits;
wherein the second subset is larger than the first subset.

24. The method of claim 20, further comprising electrically coupling at least some of the plurality of electrode pairs to a plurality of the differential measurement circuits at a same time to obtain simultaneous unipolar measurements from the plurality of electrode pairs.

25. The method of claim 15, further comprising:
dynamically switching between unipolar and bipolar modes of operation;
wherein in the unipolar mode of operation, the method further comprises, for each of a plurality of unipolar measurements, electrically coupling an active electrode and a reference electrode to one of the differential measurement circuits; and
wherein in the bipolar mode of operation, the method further comprises electrically coupling each of a plurality of electrode pairs to one of the differential measurement circuits.

* * * * *